(12) United States Patent
Trutna et al.

(10) Patent No.: US 9,904,054 B2
(45) Date of Patent: Feb. 27, 2018

(54) HEADSET WITH STRAIN GAUGE EXPRESSION RECOGNITION SYSTEM

(71) Applicant: Oculus VR, LLC, Menlo Park, CA (US)

(72) Inventors: Tristan Thomas Trutna, Seattle, WA (US); Laura Cristina Trutoiu, Seattle, WA (US); William Aaron Nicholls, Seattle, WA (US)

(73) Assignee: Oculus VR, LLC, Menlo Park, CA (US)

( * ) Notice: Subject to any disclaimer, the term of this patent is extended or adjusted under 35 U.S.C. 154(b) by 151 days.

(21) Appl. No.: 14/964,467

(22) Filed: Dec. 9, 2015

(65) Prior Publication Data

US 2016/0216760 A1    Jul. 28, 2016

Related U.S. Application Data

(60) Provisional application No. 62/106,861, filed on Jan. 23, 2015.

(51) Int. Cl.
| | |
|---|---|
| *G02B 27/01* | (2006.01) |
| *G06F 3/01* | (2006.01) |
| *A61B 5/0478* | (2006.01) |
| *A61B 5/00* | (2006.01) |

(52) U.S. Cl.
CPC .......... *G02B 27/017* (2013.01); *G06F 3/012* (2013.01); *G06F 3/015* (2013.01); *A61B 5/0478* (2013.01); *A61B 5/6803* (2013.01); *A61B 2503/12* (2013.01); *G02B 2027/014* (2013.01); *G02B 2027/0187* (2013.01)

(58) Field of Classification Search
CPC ..... G06F 3/015; G02B 27/017; A61B 5/0478; A61B 5/6803
See application file for complete search history.

(56) References Cited

U.S. PATENT DOCUMENTS

| | | | |
|---|---|---|---|
| 5,583,795 A | 12/1996 | Smyth | |
| 6,097,927 A * | 8/2000 | LaDue | ............... A61M 21/0094 434/236 |
| 8,605,008 B1 | 12/2013 | Prest et al. | |

(Continued)

OTHER PUBLICATIONS

Petrov, Y. et al., "Electric Field Encephalography as a Tool for Functional Brain Research: A Modeling Study," PloS One, Jul. 3, 2013, e67682, pages, vol. 8, No. 7.

*Primary Examiner* — Shaheda Abdin
(74) *Attorney, Agent, or Firm* — Fenwick & West LLP

(57) ABSTRACT

A head-mounted display (HMD) device includes a plurality of deformation sensors attached to a liner formed around a periphery of a HMD, adopted for direct or indirect contact a user's face. The deformation sensors measure deformations of the liner caused by movement of an upper portion of a user's face when the user is wearing the HMD. The deformation sensors are strain gauges embedded in or otherwise coupled to the liner of the HMD. The sensors translate muscle movements of the upper face of the user to changes in the bending strain and radius of curvature on the surface of the strain gauges. The HMD includes a module that reconstructs and projects a facial animation model of the user based on signals from the deformation sensors while the HMD is in use by the user.

16 Claims, 6 Drawing Sheets

(56) References Cited

U.S. PATENT DOCUMENTS

| | | | |
|---|---|---|---|
| 2002/0067362 A1* | 6/2002 | Agostino Nocera | G06K 9/00248 345/473 |
| 2006/0061544 A1* | 3/2006 | Min | G02B 27/0093 345/156 |
| 2010/0079356 A1* | 4/2010 | Hoellwarth | G02B 27/017 345/8 |
| 2010/0171680 A1* | 7/2010 | Lapidot | G02B 27/0172 345/8 |
| 2011/0234489 A1 | 9/2011 | Van Acht et al. | |
| 2012/0075168 A1* | 3/2012 | Osterhout | G02B 27/017 345/8 |
| 2013/0041292 A1* | 2/2013 | Cunningham | A61B 18/12 601/2 |
| 2013/0044128 A1* | 2/2013 | Liu | G09G 5/00 345/633 |
| 2013/0208234 A1 | 8/2013 | Lewis | |
| 2016/0077547 A1 | 3/2016 | Aimone et al. | |

\* cited by examiner

HEADSET WITH STRAIN GAUGE EXPRESSION RECOGNITION SYSTEM

CROSS REFERENCE TO RELATED APPLICATIONS

This application claims the benefit of U.S. Provisional Application No. 62/106,861, filed Jan. 23, 2015, which is incorporated by reference in its entirety.

BACKGROUND

The present invention generally relates to the field of capturing facial expressions of users wearing a head-mounted display (HMD).

The recent introduction of consumer-level HMDs has led to a revival in virtual reality and is drawing wide interest from consumers for gaming and online virtual worlds. With the help of existing motion capture and hand tracking technologies, users can navigate and perform actions in fully immersive virtual environments. But users lack a technological solution for face-to-face communication that conveys compelling facial expressions and emotions in virtual environments.

Facial animation has been mostly dominated by optical capture systems that use cameras or depth sensors. Methods for facial representations, tracking, mapping, and animation have been developed, greatly impacting film and game production. However, because a typical face is more than 60% occluded by a HMD, established optical sensing methods that achieve the desired facial tracking quality fail to capture nearly the entire upper face.

SUMMARY

Embodiments of the invention use a plurality of deformation sensors in direct or indirect contact with various different locations on an upper portion of a user's face. For example, the HMD includes a liner formed around a periphery of the HMD and adapted for direct or indirect contact with an upper portion of a user's face. The deformation sensors are attached along the liner and configured to measure deformations of the liner caused, for example, by movement of the upper portion of a user's face when the user is wearing the HMD. In one embodiment, the deformation sensors are strain gauges that translate muscle movements of the upper face of the user to changes in the bending strain and radius of curvature on the surface of the strain gauges.

The HMD is accompanied by a module that projects a facial animation model of the user from deformation sensor signals while the HMD is in use by the user. The module generates a trained model for mapping a set of deformation sensor signals to a set of animation parameters. The set of animation parameters determines the facial animation model of the user's face that is projected onto the virtual reality environment of the HMD. While the HMD is in use, the trained model is used to reconstruct a facial animation model of the user from deformation sensor signals that reflect muscle movement of the user's face. The facial animation model can then be provided to a software application being used by the user to project the user's facial expression in the virtual reality environment, among other applications.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
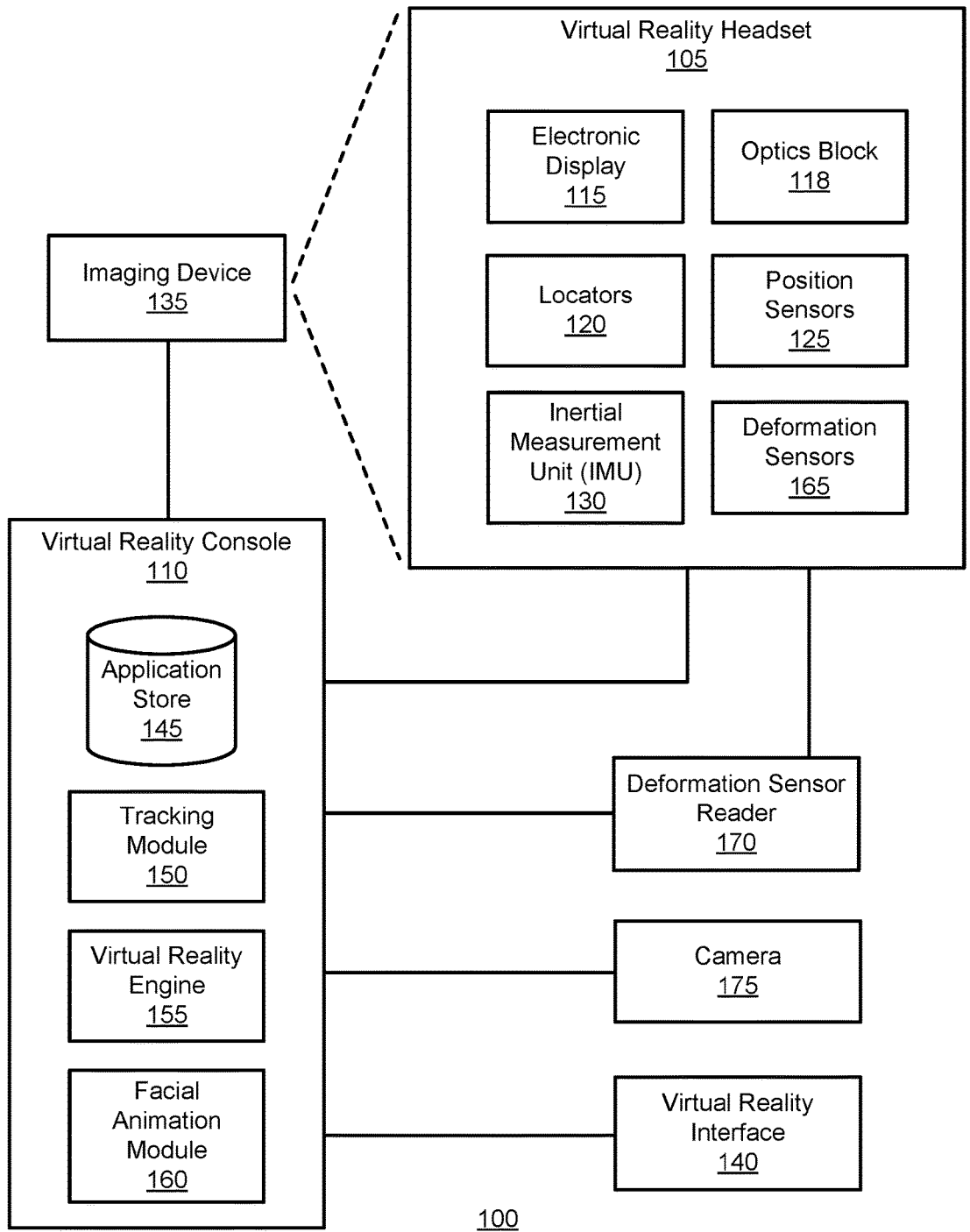
FIG. 1 is a block diagram of a system environment including a virtual reality system, in accordance with an embodiment.

FIG. 1 is a block diagram of a virtual reality (VR) system environment 100 in which a VR console 110 operates. The system environment 100 shown by FIG. 1 comprises a VR headset 105, an imaging device 135, a deformation sensor reader 170, a camera 175, and a VR input interface 140 that are each coupled to the VR console 110. While FIG. 1 shows an example system 100 including one VR headset 105, one imaging device 135, one deformation sensor reader 170, one camera 175, and one VR input interface 140, in other embodiments any number of these components may be included in the system 100. For example, there may be multiple VR headsets 105 each having an associated VR input interface 140 and being monitored by one or more imaging devices 135, with each VR headset 105, VR input interface 140, and imaging devices 135 communicating with the VR console 110. In alternative configurations, different and/or additional components may be included in the system environment 100.

The VR headset 105 is a head-mounted display (HMD) that presents media to a user. Examples of media presented by the VR head set include one or more images, video, audio, or some combination thereof. An embodiment of the VR headset 105 is further described below in conjunction with FIGS. 2 and 3. The VR headset 105 may comprise one or more rigid bodies, which may be rigidly or non-rigidly coupled to each other together. A rigid coupling between rigid bodies causes the coupled rigid bodies to act as a single rigid entity. In contrast, a non-rigid coupling between rigid bodies allows the rigid bodies to move relative to each other.

The VR headset 105 includes an optics block 118, one or more locators 120, one or more position sensors 125, an inertial measurement unit (IMU) 130, and a plurality of deformation sensors 165.

The electronic display 115 displays images to the user in accordance with data received from the VR console 110.

The optics block 118 magnifies received light, corrects optical errors associated with the image light, and presents the corrected image light to a user of the VR headset 105. In various embodiments, the optics block 118 includes one or more optical elements. Example optical elements included in the optics block 118 include: an aperture, a Fresnel lens, a convex lens, a concave lens, a filter, or any other suitable optical element that affects image light. Moreover, the optics block 118 may include combinations of different optical elements. In some embodiments, one or more of the optical elements in the optics block 118 may have one or more coatings, such as anti-reflective coatings.

The locators 120 are objects located in specific positions on the VR headset 105 relative to one another and relative to a specific reference point on the VR headset 105. A locator 120 may be a light emitting diode (LED), a corner cube reflector, a reflective marker, a type of light source that contrasts with an environment in which the VR headset 105 operates, or some combination thereof. In embodiments where the locators 120 are active (i.e., an LED or other type of light emitting device), the locators 120 may emit light in the visible band (~380 nm to 750 nm), in the infrared (IR) band (~750 nm to 1 mm), in the ultraviolet band (10 nm to 380 nm), in some other portion of the electromagnetic spectrum, or in some combination thereof.

The IMU 130 is an electronic device that generates fast calibration data indicating an estimated position of the VR headset 105 relative to an initial position of the VR headset 105 based on measurement signals received from one or more of the position sensors 125. A position sensor 125 generates one or more measurement signals in response to motion of the VR headset 105. Examples of position sensors 125 include: one or more accelerometers, one or more gyroscopes, one or more magnetometers, another suitable type of sensor that detects motion, a type of sensor used for error correction of the IMU 130, or some combination thereof. The position sensors 125 may be located external to the IMU 130, internal to the IMU 130, or some combination thereof.

The plurality of deformation sensors 165 capture facial movement of an upper portion of the user's face and are attached along a periphery of the VR headset 105. The deformation sensors 165 are in indirect or direct contact with the upper face of the user. An embodiment of the plurality of deformation sensors 165 is further described below in conjunction with FIG. 3. In one particular embodiment referred to throughout the remainder of the specification, each of the plurality of deformation sensors 165 are strain gauges in which a change in surface strain of the sensor as it is bent or flattened leads to a change in electrical resistance of the sensor. It is appreciated, however, that in other embodiments the deformation sensors 165 are alternatively and/or additionally include other sensors, such as capacitive sensors, inductive sensors, or electroencephalogram (EEG) sensors. The plurality of deformation sensors 165 may also be embedded with electrooculography (EOG) sensors for tracking and measuring eye movement of the user.

The imaging device 135 generates slow calibration data in accordance with calibration parameters received from the VR console 110. Slow calibration data includes one or more images showing observed positions of the locators 120 that are detectable by the imaging device 135. The imaging device 135 may include one or more cameras, one or more video cameras, any other device capable of capturing images including one or more of the locators 120, or some combination thereof. Additionally, the imaging device 135 may include one or more filters (e.g., for increasing signal to noise ratio). The imaging device 135 is configured to detect light emitted or reflected from locators 120 in a field of view of the imaging device 135. In embodiments where the locators 120 include passive elements (e.g., a retroreflector), the imaging device 135 may include a light source that illuminates some or all of the locators 120, which retroreflect the light towards the light source in the imaging device 135. Slow calibration data is communicated from the imaging device 135 to the VR console 110, and the imaging device 135 receives one or more calibration parameters from the VR console 110 to adjust one or more imaging parameters (e.g., focal length, focus, frame rate, ISO, sensor temperature, shutter speed, aperture, etc.).

The VR input interface 140 is a device that allows a user to send action requests to the VR console 110. An action request is a request to perform a particular action. For example, an action request may be to start or to end an application or to perform a particular action within the application. The VR input interface 140 may include one or more input devices. Example input devices include a keyboard, a mouse, a game controller, a joystick, a yoke, or any other suitable device for receiving action requests and communicating the received action requests to the VR console 110. An action request received by the VR input interface 140 is communicated to the VR console 110, which performs an action corresponding to the action request. In some embodiments, the VR input interface 140 may provide haptic feedback to the user in accordance with instructions received from the VR console 110. For example, haptic feedback is provided when an action request is received, or the VR console 110 communicates instructions to the VR input interface 140 causing the VR input interface 140 to generate haptic feedback when the VR console 110 performs an action.

The deformation sensor reader 170 is connected to each of the deformation sensors 165 and translates changes in shape or other measurement quantities of the deformation sensors 165 into electrical deformation sensor signals for use in the facial animation module 160 of the virtual reality console 110.

The camera 175 includes one or more cameras used to generate an optical map of at least a portion of the user's face. The optical map includes a plurality of optical signals corresponding to various locations of the tracked portion of the user's face. An embodiment of the camera 175 is further described below in conjunction with FIG. 5. In one particular embodiment referred to throughout the remainder of the specification, the camera 175 includes an infrared (IR) camera and a RGB-color camera, as well as an IR coded light projection system. In such an embodiment, the optical signals include a plurality of depth and image signals corresponding to various locations of the tracked portion of the user's face. It is appreciated, however, that in other embodiments the camera 175 alternatively and/or additionally includes other cameras that generate an optical map of the user's face. For example, the camera 175 may include laser-based depth sensing cameras. The camera 175 provides the optical map for use in the facial animation module 160 of the virtual reality console 110.

The VR console 110 provides content to the VR headset 105 for presentation to the user in accordance with information received from one or more of: the imaging device 135, the VR headset 105, the VR input interface 140, the deformation sensor reader 170, and the camera 175. In the example shown in FIG. 1, the VR console 110 includes an application store 145, a tracking module 150, a virtual reality (VR) engine 155, and a facial animation module 160. Some embodiments of the VR console 110 have different components than those described in conjunction with FIG. 1. Similarly, the functions further described below may be distributed among components of the VR console 110 in a different manner than is described here.

The application store 145 stores one or more applications for execution by the VR console 110. An application is a group of instructions, that when executed by a processor, generates content for presentation to the user. Content generated by an application may be in response to inputs received from the user via movement of the VR headset 105 or the VR interface device 140. Examples of applications include gaming applications, conferencing applications, video playback application, or other suitable applications.

The tracking module 150 calibrates the system environment 100 using one or more calibration parameters and may adjust one or more calibration parameters to reduce error in determination of the position of the VR headset 105. For example, the tracking module 150 adjusts the focus of the imaging device 135 to obtain a more accurate position for observed locators on the VR headset 105. Moreover, calibration performed by the tracking module 150 also accounts for information received from the IMU 130. Additionally, if tracking of the VR headset 105 is lost (e.g., the imaging device 135 loses line of sight of at least a threshold number of the locators 120), the tracking module 140 re-calibrates some or all of the system environment 100.

The VR engine 155 executes applications within the system environment 100 and receives position information, acceleration information, velocity information, predicted future positions, or some combination thereof, of the VR headset 105 from the tracking module 150. Based on the received information, the VR engine 155 determines content to provide to the VR headset 105 for presentation to the user. For example, if the received information indicates that the user has looked to the left, the VR engine 155 generates content for the VR headset 105 that mirrors the user's movement in a virtual environment. Additionally, the VR engine 155 performs an action within an application executing on the VR console 110 in response to an action request received from the VR input interface 140 and provides feedback to the user that the action was performed. The provided feedback may be visual or audible feedback via the VR headset 105 or haptic feedback via the VR input interface 140.

The facial animation module 160 projects a facial animation of a user onto the virtual reality environment while the user is wearing or using the VR headset 105. The facial animation module 160 receives deformation sensor signals from the deformation sensor reader 170 and/or an optical map of a portion of the user's face from the camera 175, and translates these signals to a facial animation model of the user for display in the virtual reality environment. An embodiment of the facial animation module 160 is described below in further detail in conjunction with FIG. 6.

Virtual Reality Headset

Figure 2:
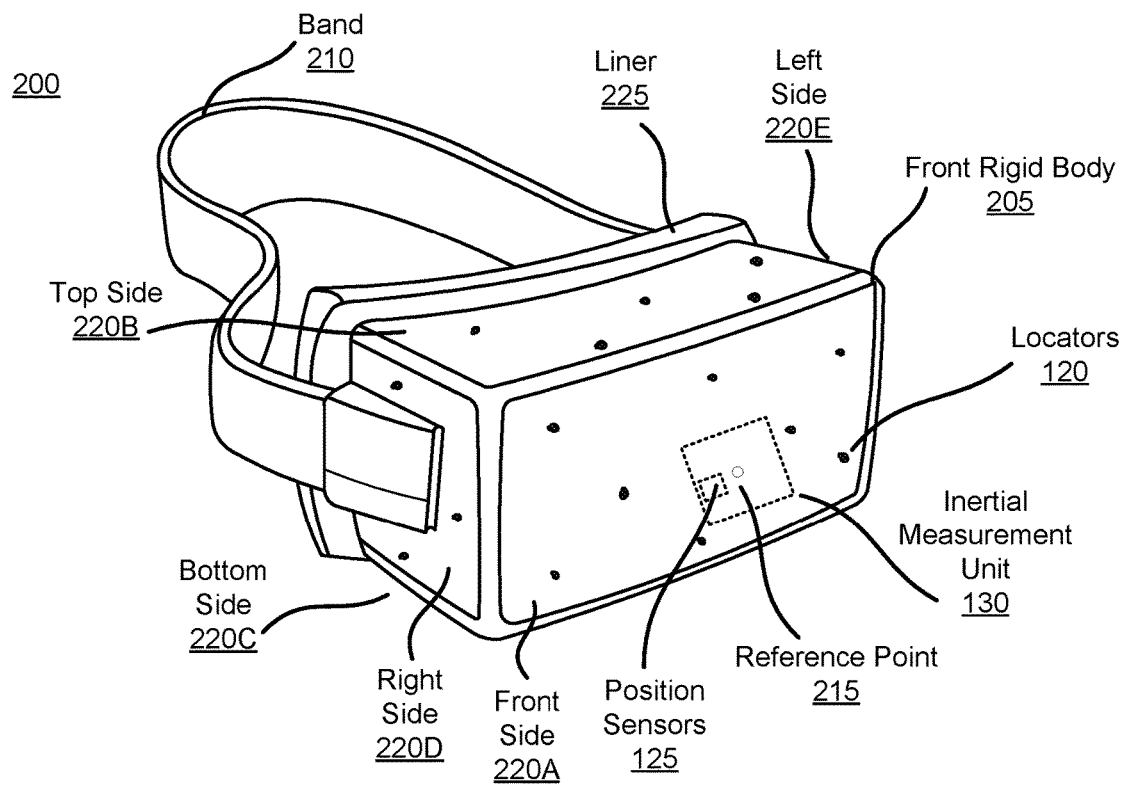
FIG. 2 is a wire diagram of a virtual reality headset, in accordance with an embodiment.

FIG. 2 is a wire diagram of a virtual reality (VR) headset 200, in accordance with an embodiment. The VR headset 200 is an embodiment of the VR headset 105, and includes a front rigid body 205 and a band 210. The front rigid body 205 includes one or more electronic display elements of the electronic display 115 (not shown), the IMU 130, the one or more position sensors 125, the locators 120, and a liner 225 around the periphery of the front rigid body 205. In the embodiment shown by FIG. 2, the position sensors 125 are located within the IMU 130, and neither the IMU 130 nor the position sensors 125 are visible to the user.

The locators 120 are located in fixed positions on the front rigid body 205 relative to one another and relative to a reference point 215. In the example of FIG. 2, the reference point 215 is located at the center of the IMU 130. Each of the locators 120 emit light that is detectable by the imaging device 135. Locators 120, or portions of locators 120, are located on a front side 220A, a top side 220B, a bottom side 220C, a right side 220D, and a left side 220E of the front rigid body 205 in the example of FIG. 2.

Figure 3:
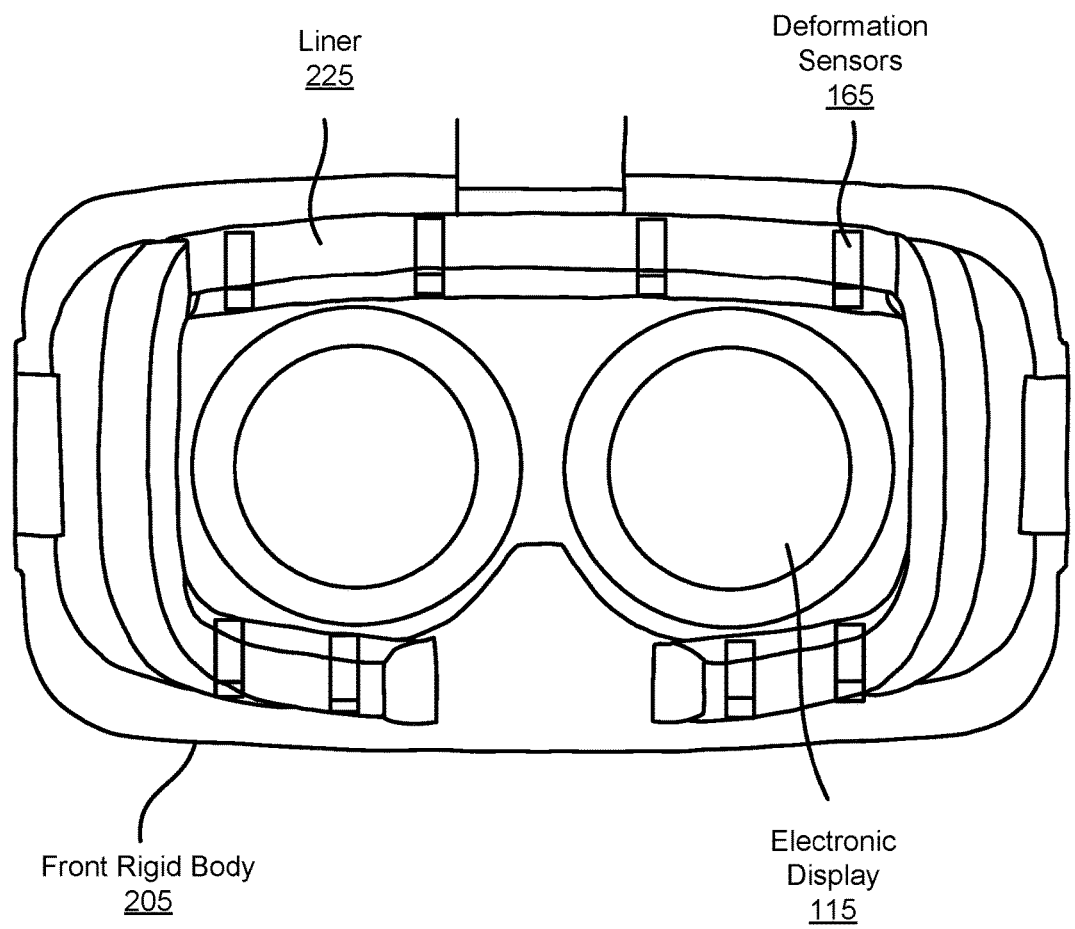
FIG. 3 is a wire diagram of an embodiment of the front rigid body of the VR headset shown in FIG. 2 having a plurality of deformation sensors, in accordance with an embodiment.

FIG. 3 is a wire diagram of an embodiment of the front rigid body 205 of the VR headset shown in FIG. 2 having a plurality of deformation sensors 165, in accordance with an embodiment. The front rigid body 205 includes a liner 225 and a plurality of deformation sensors 165 along a plurality of locations of the liner 225. The liner 225 is formed around a periphery of the front rigid body 205 of the VR headset 200. The liner 225 is adapted for direct or indirect contact with an upper portion of a user's face. In one embodiment, the liner 225 may be formed of foam. The plurality of deformation sensors 165 are securely attached along a plurality of locations along the liner 225, and capture deformations of the liner 225 caused by movement of the user's upper face when the user is wearing the VR headset 200. The degree of deformation of the liner 225 is represented by the degree of bending strain and radius of curvature of the deformation sensors 165. The bending strain and radius of curvature are directly related to the electrical resistance of the deformation sensors 165.

Deformation Sensor Reader

The deformation sensor reader 170 is connected to each of the deformation sensors 165, and includes a configuration that translates characteristic properties of the deformation sensors 165 to electrical deformation sensor signals for use in the facial animation module 160. In one embodiment, the deformation sensor reader 170 includes a plurality of three-wire Wheatstone bridge circuits connected to each of the deformation sensors 165. Each Wheatstone bridge circuit translates the bending strain or radius of curvature of a deformation sensor 165 to an output voltage of the Wheatstone bridge circuit directly related to the electrical resistance of the deformation sensor 165.

Figure 4:
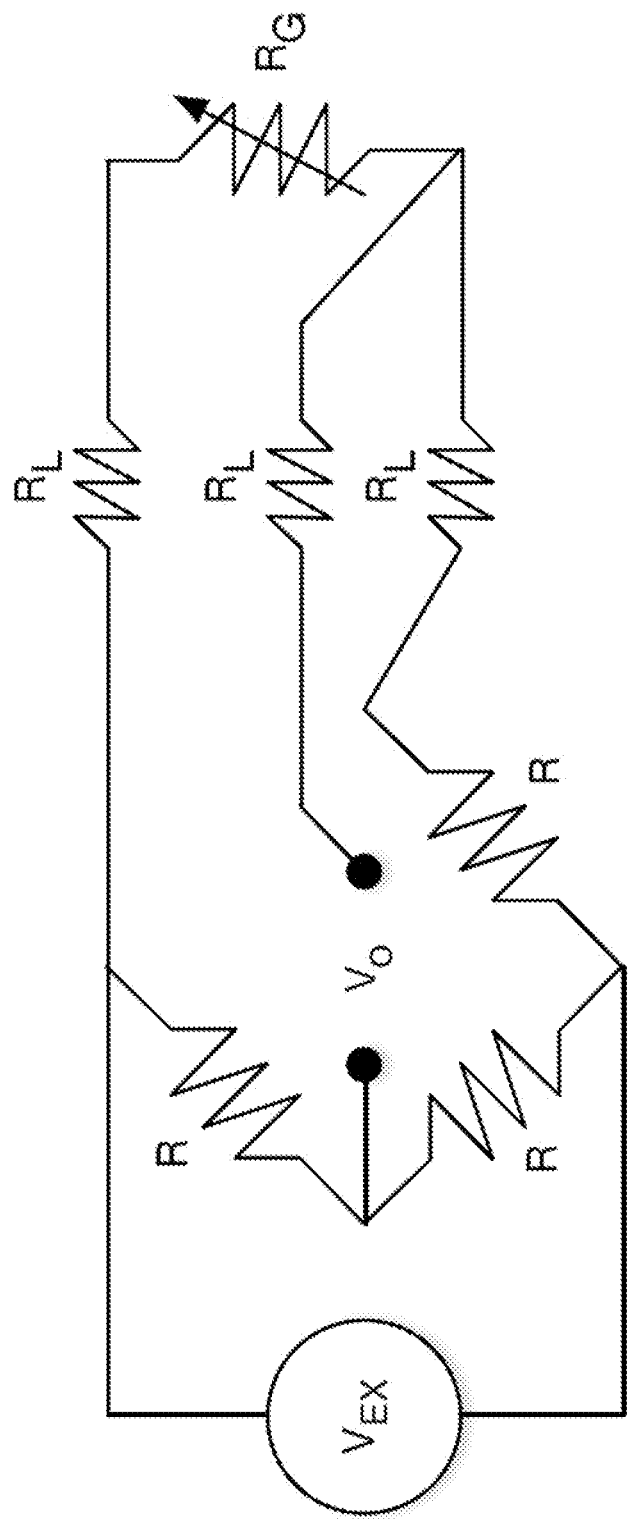
FIG. 4 is a circuit diagram showing a configuration for measuring the electrical resistance of the deformation sensors, in accordance with an embodiment.

FIG. 4 is a circuit diagram showing a three-wire Wheatstone bridge configuration used to measure the electrical resistance of the deformation sensors 165, according to one embodiment. In the circuit diagram of FIG. 4, $R_G$ denotes the resistance of a deformation sensor 165, R denotes a resistive element with a known resistance value, $R_L$ denotes the resistance of the wire, $V_{EX}$ denotes the excitation voltage, and $V_O$ denotes the measured output voltage. The output voltage $V_O$ of the Wheatstone bridge circuit as a function of the electrical resistance of the deformation sensor 165 is given by:

$$V_0 = \left(\frac{1}{2} - \frac{R_G}{R_G + R}\right) V_{EX}.$$

In such an embodiment, the deformation sensor signals are the measured output voltages $V_O$ of the Wheatstone bridge circuit. It is appreciated, however, that in other embodiments the deformation sensor reader 170 alternatively and/or additionally includes other configurations that generate deformation sensor signals based on facial movement of the user.

Depth Sensing Camera

Figure 5:
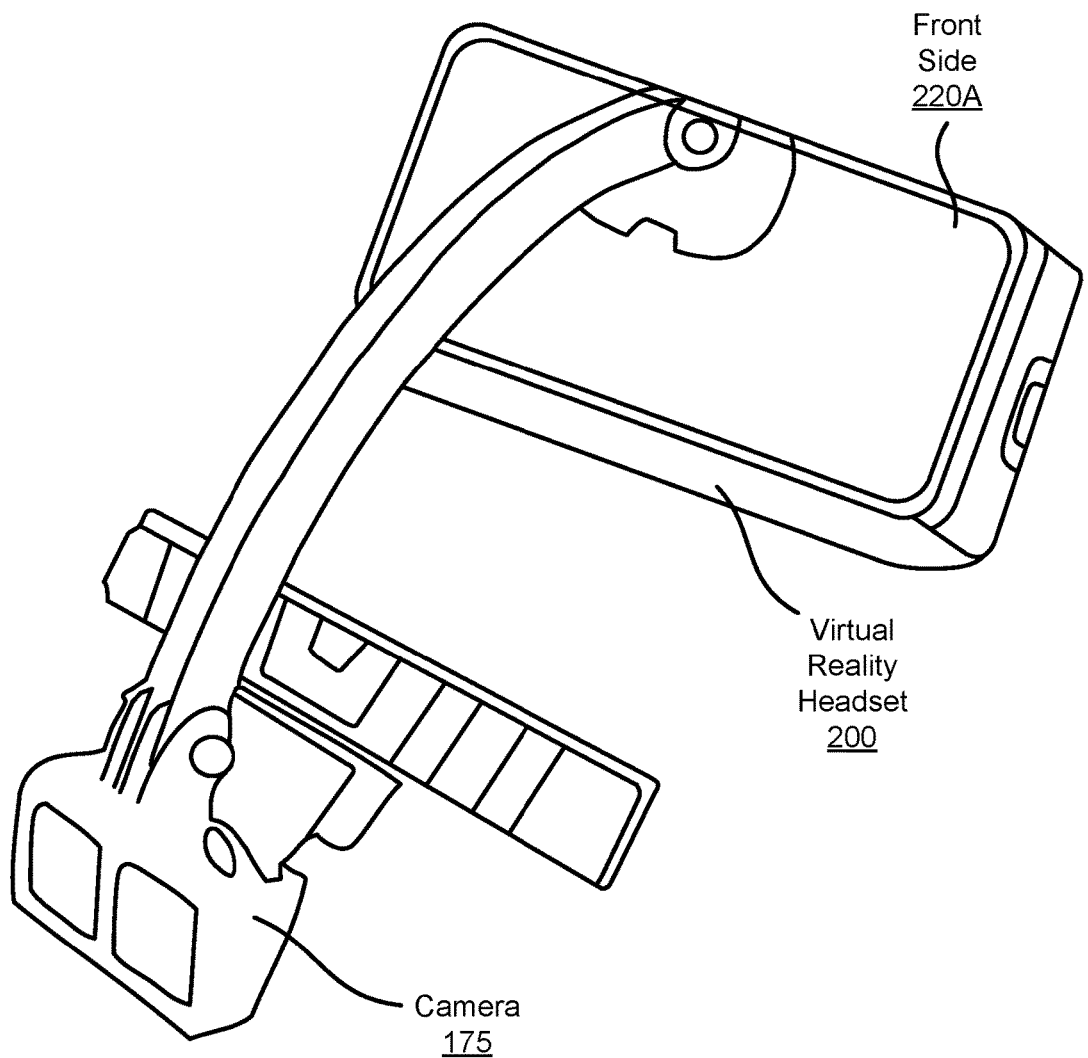
FIG. 5 is a wire diagram of a camera attached to the VR headset shown in FIG. 2, in accordance with an embodiment.

FIG. 5 is a wire diagram of an embodiment of the VR headset 200 shown in FIG. 2 with a camera 175, in accordance with an embodiment. The camera 175 tracks at least a portion of the user's face and outputs an optical map that includes a plurality of optical signals corresponding to various locations of the tracked portion of the user's face. As shown in FIG. 5, the camera 175 may be attached to a front side 220A of the VR headset 200. It is appreciated, however, that in other embodiments, the camera 175 may be attached to different sides of the VR headset 200. For example, the camera 175 may be attached to a bottom side 220C of the VR headset 200. Moreover, the camera 175 is not limited to a single camera but can also include one or more cameras attached the VR headset 200. For example, the camera 175 may include any combination of an individual RGB-color camera, an individual IR camera, or an individual depth sensing camera attached to the VR headset 200.

When the VR headset 200 is in use by the user, the camera 175 may be positioned to capture movement of the user's lower face that is not occluded by the VR headset 200, and may generate an optical map of the user's lower face. Alternatively, when the VR headset 200 is not in use, the camera 175 may be positioned to capture movement of the user's full face, and may generate an optical map of the user's full face.

Facial Animation Module

Figure 6:
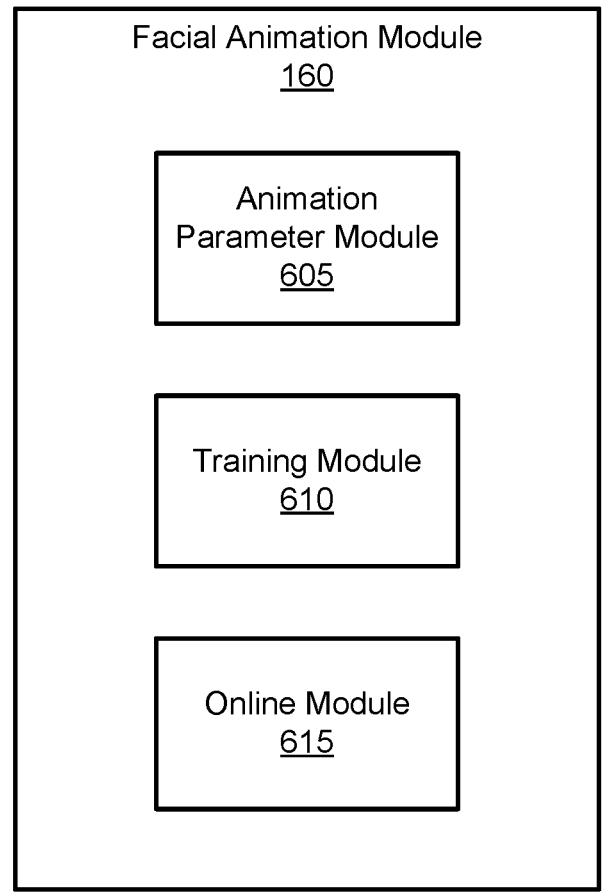
FIG. 6 is a block diagram illustrating the facial animation module implemented by the virtual reality console, in accordance with an embodiment.

FIG. 6 is a block diagram illustrating the facial animation module 160 implemented by the virtual reality console 110, in accordance with an embodiment. The facial animation module 160 includes an animation parameter module 605, a training module 610, and an online module 615. Some embodiments of the facial animation module 160 have different and/or additional modules than the ones described here. Similarly, the functions can be distributed among the modules in a different manner than is described here. Certain modules and functions can be incorporated into other modules of the facial animation module 160 and/or other entities on the virtual reality console 110.

The animation parameter module 605 extracts animation parameters from optical maps received from the camera 175. The extracted animation parameters are used to generate a facial animation model of the tracked portion of the user's face. For example, animation parameters may be extracted from an optical map of a lower face of the user to generate a facial animation model of the lower face of the user. In one embodiment, the facial animation model is a blendshape model that models a user's facial expression by a linear combination of key expression meshes identified for the user. In such an embodiment, the extracted animation parameters are a vector of blendshape coefficients that determine the weight of each expression mesh in the linear combination. The blendshape coefficients may be extracted real-time by any suitable method, such as that described in Li et al. in "Realtime facial animation with on-the-fly correctives," 2013, *ACM Transactions on Graphics, Proceedings of the* 40*th ACM SIGGRAPH Conference and Exhibition* 2013, Vol. 32, No. 4, which is incorporated herein by reference in its entirety.

The training module 610 generates a trained model that maps deformation sensor signals and/or extracted animation parameters of a portion of a user's face to estimated animation parameters of a user's full face. For example, the portion of the user's face may be a lower face part of the user, including the lip region. The estimated animation parameters of the user's full face are then used to display a facial animation model of the user in the virtual reality environment. The training module 610 may use only the deformation sensor signals, only the extracted animation parameters of a portion of the user's face, or a combination of both signals to estimate animation parameters of the user's full face. The trained model allows estimation of a user's full facial animation model when part of the user's face is occluded by the VR headset 200.

The online module 615 receives deformation sensor signals from the deformation sensor reader 170 and/or an optical map of a portion of a user's face from the camera 175 and reconstructs a full facial animation model of the user using the trained model from the training module 610, while the VR headset 200 is in use. The trained model outputs a set of animation parameters for the user's full face that determines the facial animation model of the user for display in the virtual reality environment.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A head-mounted display device comprising:
   a headset;
   a display panel for displaying a virtual environment, the display panel attached to the headset and positioned in front of a upper face part of the user;
   a liner formed around a periphery of the headset, the liner adapted for direct or indirect contact with an upper portion of a user's face and configured to change a shape in response to movements of the upper portion of the user's face; and
   a plurality of sensors attached along a plurality of locations of the liner that capture deformations of the liner caused by the movements of the upper portion of the user's face when the user is wearing the head-mounted display device, the deformations of the liner resulting in a degree of bending and a change in a radius of curvature associated with the plurality of sensors.

2. The head-mounted display device of claim 1, further comprising one or more cameras attached to the device and positioned to capture a lower portion of the user's face that is not occluded by the head-mounted display device.

3. The head-mounted display device of claim 1, wherein the plurality of sensors comprise strain gauges.

4. The head-mounted display device of claim 1, wherein the plurality of sensors comprise capacitive sensors.

5. The head-mounted display device of claim 1, wherein the plurality of sensors comprise inductive sensors.

6. The head-mounted display device of claim 1, wherein the plurality of sensors comprise electroencephalogram (EEG) sensors.

7. The head-mounted display device of claim 1, wherein the liner comprises foam.

8. A method of capturing facial performance of a user with a head-mounted display device, the method comprising:
   collecting deformation signals of a liner of the head-mounted display device using a plurality of sensors on a plurality of locations on the liner, wherein the liner is configured to change a shape in response to movements of an upper portion of a user's face when the user is wearing the head-mounted display device, and the deformation signals detect a degree of bending and a change in a radius of curvature associated with the plurality of sensors;
   generating a set of animation parameters by applying a model to the deformation signals; and
   inputting the generated animation parameters to a computer software system that drives a display panel of the head-mounted display device for projecting a facial animation model of the user's face to the display panel.

9. The method of claim 8, further comprising:
   collecting optical signals of a lower portion of the user's face, wherein the optical signals are obtained by one or more cameras attached to the head-mounted display device positioned in front of the lower portion of the user's face that is not occluded by the head-mounted display device; and
   generating the set of animation parameters by applying the model to the deformation signals and the optical signals.

10. The method of claim 8, wherein the facial animation model is a blendshape model that linearly combines a plurality of expression meshes, and the facial animation parameters are a sequence of blendshape coefficients that correspond to a weight of each expression mesh in the linear combination.

11. The method of claim 8, wherein the facial animation parameters are skeletal animation controls.

12. The method of claim 8, wherein the plurality of sensors comprise strain gauges.

13. The method of claim 8, wherein the plurality of sensors comprise capacitive sensors.

14. The method of claim 8, wherein the plurality of sensors comprise inductive sensors.

15. The method of claim 8, wherein the plurality of sensors comprise electroencephalogram (EEG) sensors.

16. The method of claim 8, wherein the liner comprises foam.

* * * * *